US006656883B1

(12) United States Patent
Vogt et al.

(10) Patent No.: US 6,656,883 B1
(45) Date of Patent: Dec. 2, 2003

(54) WETTABLE POWDER FORMULATIONS OF HERBICIDES

(75) Inventors: Manfred Vogt, Bad Säckingen (DE); Manfred Hudetz, Greensboro, NC (US)

(73) Assignee: Syngenta Investment Corp., Wilmington, DE (US)

( * ) Notice: Subject to any disclaimer, the term of this patent is extended or adjusted under 35 U.S.C. 154(b) by 0 days.

(21) Appl. No.: 08/669,513

(22) PCT Filed: Jan. 3, 1995

(86) PCT No.: PCT/IB95/00001

§ 371 (c)(1),
(2), (4) Date: Nov. 19, 1996

(87) PCT Pub. No.: WO95/18531

PCT Pub. Date: Jul. 13, 1995

(30) Foreign Application Priority Data

Jan. 10, 1994 (CH) ................................... 64/94

(51) Int. Cl.⁷ ....................... A01N 25/30; A01N 43/40; A01N 43/60; A01N 47/36
(52) U.S. Cl. ....................... 504/105; 504/110; 504/235; 504/258; 504/270; 504/323; 504/358
(58) Field of Search ................. 504/110, 105, 504/235, 258, 270, 323, 358

(56) References Cited

U.S. PATENT DOCUMENTS

| | | | |
|---|---|---|---|
| 4,419,121 A | 12/1983 | Meyer et al. ................ | 71/92 |
| 4,425,154 A | 1/1984 | Meyer et al. ................ | 71/92 |
| 4,505,743 A | 3/1985 | Schurter et al. ............. | 71/94 |
| 4,671,819 A | 6/1987 | Meyer et al. ................ | 71/93 |
| 4,713,109 A | 12/1987 | Schurter et al. ............. | 71/94 |
| 4,759,793 A | 7/1988 | Meyer et al. ................ | 71/92 |
| 4,881,966 A | 11/1989 | Nyffeler et al. ............. | 71/94 |
| 4,936,899 A | 6/1990 | Schulz et al. ............... | 71/73 |
| 5,023,333 A | 6/1991 | Hubele ....................... | 546/175 |
| 5,102,445 A | 4/1992 | Hubele ....................... | 71/94 |
| 5,129,944 A * | 7/1992 | Andree et al. ............... | 71/98 |
| 5,171,352 A | 12/1992 | Grossmann et al. .......... | 71/72 |

FOREIGN PATENT DOCUMENTS

| | | |
|---|---|---|
| EP | 0044807 | 1/1982 |
| EP | 0094349 | 11/1983 |
| EP | 0190995 | 8/1986 |

OTHER PUBLICATIONS

Derwent Abstract 86–212873/33 (of DE 3503–706–A) 1986.
WSSA Abstract, 1992 Meeting of the Weed Science Society of America, vol. 32, 1992, p. 13.
Weed Science, vol. 42, 1994, pp. 1–4.

* cited by examiner

*Primary Examiner*—S. Mark Clardy
(74) *Attorney, Agent, or Firm*—William A. Teoli, Jr.

(57) ABSTRACT

A formulation comprising:
  a) a herbicide,
  b) a porous solid carrier, and
  c) 30–60% by weight of a nonionic surfactant of formula I:

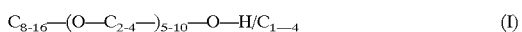

$$C_{8-16}-(O-C_{2-4}-)_{5-10}-O-H/C_{1-4} \quad \text{(I)}$$

The herbicides may be selected from the group consisting of urea herbicides, imidazolinones, sulfonylureas, uracils, cyclohexanediones, chloroacetanilides, oxime ethers, triazines, or phenoxypropionic acid herbicides, in particular, the phenoxypropionic acid derivatives:
  (III) clodinafop-propargyl
  (IV) propaquizafop
  (V) fluazifop-butyl
  (VI) fenoxaprop-ethyl
  (VII) quizalofop-ethyl
optionally in combination with the safener (VIII) cloquintocet-mexyl.

18 Claims, No Drawings

WETTABLE POWDER FORMULATIONS OF HERBICIDES

This application has been filed under 35 USC 371 as the National stoge of International application PCT/IB95/00001, filed Jan. 3, 1995.

The present invention relates to a wettable powder formulation of solid herbicides on a solid carrier material and large amounts of a nonionic surfactant which is a reaction product of an alcohol with longer chain length and identical or different alkylene oxides, and whose end groups may additionally be alkylated.

Pesticides are usually marketed as formulated concentrates. In addition to water-dispersible powders, it is also possible to use suspension concentrates, emulsifiable concentrates or other physical forms, as described, inter alia, in EP-B-0 190 995. Emulsifiable concentrates consist essentially of a concentrated solution of the active ingredient in a suitable organic solvent, typically a mineral oil or xylene, which can be emulsified in water by adding suitable surfactants. They usually have very good biological activity and are easily to handle when formulating the spray mixture. One disadvantage is the use of an organic solvent.

Water-dispersible and wettable powders typically consist of inert carrier materials, one or more active ingedients, and surface active compounds that ensure easily wettability with water. Organic solvents are not required. It is frequently observed that these powders have a markedly lower biological activity than emulsifiable concentrates, so that this type of formulation is impracticable, i.e. it must be used in too high concentration.

Nonionic surfactants derived from fatty alcohol ethoxylates may also be used for formulating wettable powders. Usually, however, only minor amounts of surfactant are used, as the powders are required to be readily flowable and must remain storage-stable over a considerable period of time. On contact with water, no lumps shall form and the powder must form a fine dispersion as rapidly as possible when stirred in water.

C. L. McGiness, P. J. Porpiglia and G. R. Gillespie report in Abstr. Meet. Weed Sci. Soc. Am. (32, 13, 1992) on greater biological control when using primisulfuron in admixture with ethoxylated fatty alcohols. The fatty alcohol ethoxylate preferably consists of a 70% ethoxylated $C_{12}$–$C_{14}$ fatty alcohol. The fatty alcohol ethoxylate is mixed direct with the herbicide, the mixture is diluted with water and then applied in a greenhouse.

A wettable powder useful in practice having a high content of fatty alcohol ethoxylate and very good biological properties has so far not been disclosed.

It has now been found that storage-stable wettable powders of high biological activity can be obtained by applying herbicidally active compounds together with large amounts of an alkylene-oxylated alcohol with longer chain length as nonionic surfactant on a solid porous carrier material, even if said nonionic surfactant carries alkylated end groups. Accordingly, in one of its aspects the invention relates to a formulation comprising
  a) at least one herbicide,
  b) at least one porous solid carrier material, and
  c) a nonionic surfactant,
which formulation contains 30 to 60% by weight, based on the total formulation, of at least one nonionic surfactant of formula I $$R_1-(O-R_2-)_nO-R_3 \quad \text{(I)}$$

wherein $R_1$ is $C_8$–$C_{16}$alkyl or $C_8$–$C_{16}$alkenyl, $R_2$ is identical or different $C_2$–$C_4$alkylene, $R_3$ is hydrogen or $C_1$–$C_4$alkyl, and n is an integer from 5–10.

Suitable herbicides are known per se and described, inter alia, in R. Wegler, Chemie der Pflanzenschutz-und Schädlingsbekämpfungsmittel (Chemistry of Plant Protection Agents and Pesticides), Volume 2, Springer Verlag 1970, pp. 196–390.

Preferred herbicides are those selected from the groups consisting of the urea derivatives, imidazolinones, sulfonylureas, uracils, cyclohexanediones, chloroacetanilides, oxime ethers, triazines and phenoxypropionic acid derivatives.

Particularly preferred herbicides are those of the group of phenoxypropionic acid derivatives disclosed, inter alia, in EP 0 083 556. They are particularly useful active ingredients for the wettable powders of this invention.

Another preferred group of herbicides is that of the group of the sulfonylureas disclosed, inter alia, in EP-A-0 044 807 or in EP-A-0 120 814.

The novel formulations may additionally comprise safeners, typically those of the group of the quinoline derivatives. Particularly preferred safener-herbicide combinations are disclosed, inter alia, in EP-A-0 191 736 or in EP-A-0 094 349.

Particularly preferred herbicides are compounds of formula II which may be in the form of the R enantiomer or the racemate

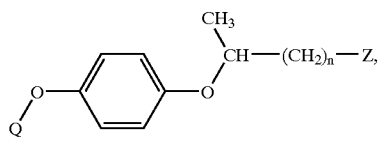

II wherein Q is a radical of formula

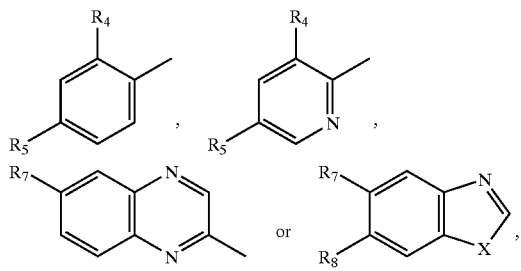

wherein $R_4$ is hydrogen, F, Cl or Br;
$R_5$ is $CF_3$, CN, Cl, Br or I;
$R_7$ and $R_8$ are each independently of the other F, Cl, Br, I, $CF_3$ or CN,
X is oxygen or sulfur, and n is 0 or an integer from 1 to 3;
Z is a radical of formula

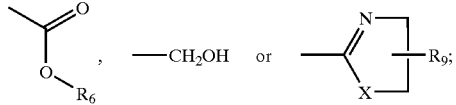

wherein $R_6$ is hydrogen, $C_1$–$C_8$alkyl, $C_3$–$C_8$alkenyl, $C_3$–$C_8$alkynyl, $C_1$–$C_8$haloalkyl, $C_3$–$C_8$haloalkenyl, $C_3$–$C_8$haloalkynyl, or $C_1$–$C_6$alkyl which is substituted by CN, $NO_2$, $C_1$–$C_4$alkoxy, $C_1$–$C_4$alkyl-SO—, $C_1$–$C_4$alkyl-$SO_2$—, $C_1$–$C_8$alkoxycarbonyl, $C_3$–$C_8$alkenyloxycarbonyl, $C_3$–$C_8$alkynyloxycarbonyl, $C_1$–$C_4$alkylidene-aminooxy or $N(R_{10})(R_{11})$, or is $C_3$–$C_8$alkenyl;

$R_9$ alkyl, haloalkyl, CN or $C_1$–$C_4$alkoxycarbonyl;

and $R_{10}$ and $R_{11}$ are each independently of the other $C_1$–$C_8$alkyl, $C_3$–$C_8$alkenyl, $C_3$–$C_8$alkynyl, phenyl, benzyl or phenyl or benzyl, each substituted by halogen, $NO_2$, CN, $OCH_3$, or $CF_3$, or $R_{10}$ and $R_{11}$, together with the linking nitrogen atom, form a 5–7-membered saturated heterocycle.

Alkyl in $R_6$, $R_9$, $R_{10}$ and $R_{11}$ may be linear or branched and, in the significance of $C_1$–$C_8$alkyl, is typically ethyl, the different isomers of propyl, butyl, pentyl, hexyl, heptyl or octyl.

Alkenyl in $R_6$, $R_{10}$ and $R_{11}$ may be linear or branched and in the significance of $C_3$–$C_8$alkenyl is typically the different isomers of propenyl, butenyl, pentenyl, hexenyl, heptenyl or octenyl. Alkenyl is preferably $C_2$–$C_7$alkenyl-$CH_2$—.

Alkynyl may be linear or branched and in the significance of $C_3$–$C_8$alkynyl is typically the different isomers of propynyl, butynyl, pentynyl, hexynyl, heptynyl or octynyl. Alkynyl is preferably $C_2$–$C_7$alkynyl-$CH_2$—, $C_1$–$C_4$Alkoxy is typically methoxy, ethoxy, propoxy or butoxy. $C_1$–$C_4$Alkylthio may be methylthio, ethylthio, propylthio or butylthio.

The 3–8-membered N-heterocycle is preferably morpholino or piperidino.

Very particularly preferred herbicides are compounds of formula III or IV (III)

(IV)

especially in the R-configuration.

Further preferred compounds are those of formula V, VI or VII.

(V)

(VI)

(VII)

Suitable safeners are a number of the quinoline derivatives disclosed in the references cited hereinabove. A compound of formula (VIII)

is particularly suitable.

The aforementioned compounds of Formulae III–VIII have the following common names in the art:

III clodinafop-propargyl
IV propaquizafop
V fluazifop-butyl
VI fenoxaprop-ethyl
VII quizalofop-ethyl
VIII cloquintocet-mexyl.

The herbicides can be used in an amount of 1 to 30% by weight, preferably of 5 to 15%, based on the entire formulation.

If a safener is concurrently used, the ratio of safener to herbicide is 1:5 to 5:1, preferably 1:4 to 1:1.

Herbicide and safener usually have an average particle size of 1:100, preferably of 1:50 and, most. preferably, of 1 to 25 μm.

The solid carriers are porous and preferably have an inner surface area of at least 10 m²/g, preferably 20 to 400 m²/g and, most preferably, 20 to 200 m²/g. Solid carriers for wettable powders are usually natural mineral fillers such as calcite, talcum, kaolin, diatomaceous earth, montmorillonite or attapulgite. In order to improve the physical properties it is also possible to add highly dispersed silicic acid, synthetic highly absorbent silicic acid, or porous polymers such as urea/formaldehyde condensate (Pergopak). Suitable granulated adsorptive carriers are porous types such as pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues. The carrier material usually has an average particle size of 1 to 200 μm, preferably 1 to 100 μm and, most preferably, 1 to 25 μm. The particle size of plant residues is usually larger and can be up to 500 μm.

The porous carrier material is preferably used in an amount of 30 to 60% by weight, most preferably 35 to 50% by weight, based on the total formulation. The percentages in connection with the formulation make up 100%.

$R_1$ in formula I is preferably $C_{10}$–$C_{15}$alkyl and, most preferably, $C_{12}$–$C_{14}$alkyl. Alkyl may be linear or branched and is preferably linear. Alkyl may be mixtures of alkyl radicals with different chain lengths. Typical examples are octyl, nonyl, decyl, undecyl, dodecyl, tridecyl, tetradecyl, pentadecyl and hexadecyl.

n in formula I is preferably an integer from 6 to 8. The compounds of formula I are preferably technical mixtures that contain oligomers in which n=5–10, preferably n=6–8.

$R_2$ is typically ethylene, 1,2-propylene or 1,2-butylene. If $R_2$ denotes different alkylene radicals, the compounds may be random or block oligomers.

$R_2$ is typically a mixture of $C_2$alkylene and $C_4$alkylene and $R_3$ is hydrogen or methyl.

Most preferably $R_1$ is $C_{10}$–$C_{15}$alkyl, $R_2$ is $C_2$alkylene, $R_3$ is hydrogen and n is an integer from 6 to 8.

The novel formulations may additionally comprise other surface-active compounds, conveniently in an amount of 1 to 15% by weight, preferably 1 to 10% by weight, based on the total formulation.

Depending on the type of active ingredient or combination of active ingredients to be formulated, suitable surface-active compounds are nonionic, cationic and/or anionic surfactants having good emulsifying, dispersing and wetting properties. Surfactants will also be understood as comprising mixtures of surfactants.

Suitable anionic surfactants may be water-soluble soaps as well as water-soluble synthetic surface-active compounds.

Suitable soaps are the alkali metal salts, alkaline earth metal salts, ammonium salts or substituted ammonium salts of higher fatty acids ($C_{10}$–$C_{22}$), e.g. the sodium or potassium salts of oleic or stearic acid, or of mixtures of natural fatty acids which can be obtained, inter alia, from coconut oil or tall oil. Further suitable soaps are also the fatty acid methyl taurin salts.

More often, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts, ammonium salts or substituted ammonium salts, and they contain a $C_8$–$C_{22}$alkyl radical which also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Corresponding phosphates, typically salts of the phosphoric acid ester of an adduct of p-nonylphenol with 4 to 14 mol of ethylene oxide, or phospholipids, are also suitable.

Further suitable nonionic surfactants are preferably polyglycol ether derivatives of aliphatic or cycloaliphatic alcohols or of saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenol polyethoxylates, polyethoxylated castor oil, polyadducts of polypropylene and polyethylene oxide, tributylphenol polyethoxylate, polyethylene glycol and octylphenol polyethoxylate. Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl) ethylammonium bromide.

The surfactants customarily employed in the art of formulation are described, inter alia, in "Mc Cutcheon's Detergents and Emulsifiers Annual", MC Publishing Corp., Glen Rock, N.J., 1981, H. Stache, "Tensid-Taschenbuch" (Handbook of Surfactants), Carl Hanser Verlag, Munich/Vienna 1981, and M. and J. Ash. "Encyclopedia of Surfactants", Vol. I–III, Chemical Publishing Co., New York, 1980–1981.

The compositions are prepared in known manner, e.g. by homogeneously mixing and/or grinding the active ingredients with extenders, typically with solvents, solid carriers and, in some cases, surface-active compounds (surfactants).

Mixing can be carried out in ordinary commercial mixers. If the active ingredients have a low melting point, it is expedient to premix a portion of the carrier material with the total amount of herbicide and the safener, if used, and to grind the mixture, then to add the rest of the carrier material and, finally, to add the surfactant useful in the practice of this invention and other optional adjuvants.

It is usually often possible to mix the carrier loaded with the surfactant with the herbicide and afterwards to grind the mixture.

If the active ingredients have higher melting points, components (a) and (b) are conveniently mixed in the finely ground state or ground together and component (c) is then added.

The end user will normally use the active ingredient concentrates or wettable powders in the form of dilute compositions. This is done by dispersing a biologically active amount of the formulation in water.

The invention therefore also relates to a composition for controlling weeds and grasses in crops of cultivated plants, which composition contains a biologically effective amount of the novel formulation in water.

The amount of formulation added to water to prepare a spray mixture will depend on the type of application. Usually a 0.1 to 10% by weight aqueous dispersion is prepared.

Suitable cultivated plants are preferably those which are important in the food or textile sector, typically sugar cane and, in particular, millet, maize, rice and cereals (wheat, rye, barley, oats). The use of the novel composition in crops of cereals is very particularly preferred.

The weeds to be controlled can be both monocot as well as dicot weeds.

The concentration of herbicide will usually be from 0.001 to 1 kg/ha, but preferably from 0.01 to 0.5 kg a.i./ha. In postemergence treatment of the weeds, a reduction of 80 to 98% of biomass is usually achieved.

Application of these compositions may be spraying, atomising, coating or drenching.

The invention also relates to a method of selectively controlling weeds, which comprises treating crops of cultivated plants, the seeds or the crop area thereof with an effective amount, usually from 0.01 to 0.5 kg/ha, of a herbicidal composition contains the herbicidal formulation of this invention, preferably using water as diluent.

The invention further relates to the use of nonionic surfactants of formula I for the preparation of wettable powder formulations for use as herbicidal compositions.

The invention is illustrated by the following Examples.

A) FORMULATION EXAMPLES

A premix comprising about 20% by weight of herbicide and 5% by weight of safener is prepared from the total amount of herbicider and safener in a mixing and milling apparatus with a portion of the carrier material. The remainder of the carrier material is then added and then the surfactant is applied. Afterwards the solid dispersants are added and a homogeneous mixture is prepared. The formulations are described in the following Examples. All percentages are by weight. The suspensibility of the wettable powders indicated in Examples A4 to A6 is determined in accordance with the method laid down in CIPAC MT 15.1.

Example A1

Formulation of a Wettable Powder

8% of compound of formula III
2% of compound of formula VIII
3% of sodium butylnaphthalenesulfonate
5% of sodium ligninsulfonate
44% of isotridecanol-8-ethoxylate (Gezetol 138®)
38% of highly dispersed urea-formaldehyde polycondensate (Pergopak® M)

Example A2

Formulation of a Wettable Powder

4% of compound of formula III
1% of compound of formula VIII
1.5% of sodium butylnaphthalenesulfonate
2.5% sodium ligninsulfonate
55% of isotridecanol-8-ethoxylate
36% highly dispersed urea-formaldehyde polycondensate

Example A3

Formulation of a Wettable Powder

8% of compound of formula III
2% of compound of formula VIII
2% of epoxidised soybean oil
1.5% of sodium butylnaphthalenesulfonate
2.5% of sodium ligninsulfonate
42% of terminally alkylated fatty alcohol alkoxylate (Plurafac® LF 431)
42% of highly dispersed urea-formaldehyde polycondensate

Example A4

Formulation of a Wettable Powder 35.0% of compound of formula IV
1.1% of sodium lauryl sulfate
3.0% of sodium ligninsulfonate
20.9% of precipitated silicic acid
40.0% of isotridecanol 8 EO The initial suspensibility is 70% and after storage for 6 months at room temperature is still 65%.

Example A5

Formulation of a Wettable Powder 30.0 g of compound of formula IV
1.1 g of sodium lauryl sulfate
3.0 g of sodium ligninsulfonate
22.5 g of precipitated silicic acid
1.9 g of pyrogenic silic acid
40.0 g of isotridecanol 8 EO
1.5 g of calcined diatomaceous earth The initial suspensibility is 90% and after storage for 6 months at room temperature is still 85%.

Example A6

Formulation of a Wettable Powder 25.0 g of compound of formula IV
0.9 g of sodium lauryl sulfate
2.5 g of sodium ligninsulfonate
28.3 g of calcium silicate
1.6 g of pyrogenic silicic acid
40.0 g of isotridecanol 8 EO
1.7 g of calcined diatomaceous earth The initial suspensibility is 74% and after storage for 6 months at room temperature is still 70%.

The following Examples illustrate the biological activity of such dispersions.

B) APPLICATION EXAMPLES

Example B1

Postemergence Herbicidal Action

An aqueous dispersion of the formulation of Example A1 is sprayed in different concentrations, expressed in g of active ingredient per hectare, onto the plants in a greenhouse trial. The plants are then kept at 20° C. and 45–60% relative humidity and regularly watered. The trials are evaluated visually 23 days after treatment. The following species of grass are treated: Avena fatua, Lolium perenne. For control purposes, the wheat variety Arina is treated concurrently.

The result is shown Table 1.

TABLE 1

| Relative damage in % to untreated control plants (visual assessment of the reduction of biomass) | | | |
|---|---|---|---|
| | Concentration (g of active ingredient/ha) | | |
| | 40 | 20 | 10 |
| "Arina" wheat | 0 | 0 | 0 |
| Alopecurus | 95 | 90 | 30 |
| Avena | 95 | 75 | 0 |
| Lolium | 80 | 60 | 20 |

What is claimed is:

1. A formulation comprising
   a) at least one herbicide,
   b) at least one porous solid carrier material, and
   c) 30 to 60% by weight, based on the total formulation, of at least one nonionic surfactant of formula I

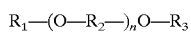

wherein $R_1$ is $C_8$–$C_{16}$alkyl or $C_8$–$C_{16}$alkenyl, $R_2$ is identical or different $C_1$–$C_4$alkylene, $R_3$ is hydrogen or $C_1$–$C_4$alkyl, and n is an integer from 5–10.

2. A formulation according to claim 1, wherein $R_1$ is $C_{10}$–$C_{15}$alkyl.

3. A formulation according to claim 1, wherein $R_2$ is a mixture of $C_2$alkylene and $C_4$alkylene, and $R_3$ is hydrogen or methyl.

4. A formulation according to claim 1, wherein $R_2$ is $C_2$alkylene, $R_3$ is hydrogen, and n is an integer from 6 to 8.

5. A formulation according to claim 1, wherein the solid carrier material is selected from the group consisting of calcite, talcum, kaolin, montmorillonite, attapulgite, sepiolite, bentonite, highly dispersed silicic acid, synthetic highly absorbent silicic acid, and a highly dispersed urea/formaldehyde polycondensate.

6. A formulation according to claim 1, wherein the herbicide is selected from the group consisting of the group of the urea derivatives, imidazolinones, sulfonylureas, uracils, cyclohexanediones, chloroacetanilides, oxime ethers, triazines or phenoxypropionic acid derivatives.

7. A formulation according to claim 1, which additionally comprises a safener selected from the group of the quinoline derivatives.

8. A formulation according to claim 6, which comprises a herbicide selected from the group of the phenoxypropionic acid derivatives.

9. A formulation according to claim 1, wherein the herbicide component (a) is a compound of formula II and is used in the form of the R enantiomer or the racemate

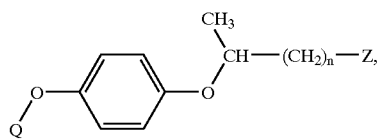

(II)

wherein Q is a radical of formula

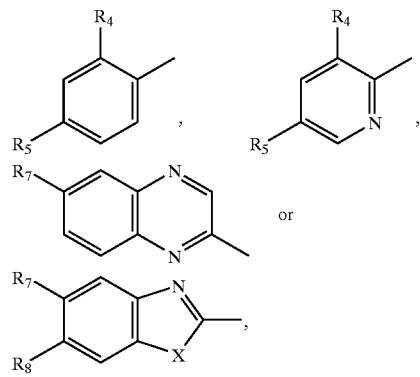

wherein $R_4$ is hydrogen, F, Cl or Br;

$R_5$ is $CF_3$, CN, Cl, Br or I;

$R_7$ and $R_8$ are each independently of the other F, Cl, Br, I, $CF_3$ or CN,

X is oxygen or sulfur, and n is 0 or an integer from 1 to 3;

Z is a radical of formula

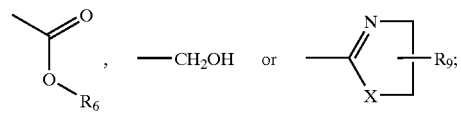

wherein $R_6$ is hydrogen, $C_1$–$C_8$alkyl, $C_3$–$C_8$alkenyl, $C_3$–$C_8$alkynyl, $C_1$–$C_8$haloalkyl, $C_3$–$C_8$haloalkenyl, $C_3$–$C_8$haloalkynyl, or $C_1$–$C_6$alkyl which is substituted by CN, $NO_2$, $C_1$–$C_4$alkoxy, $C_1$–$C_4$alkyl-SO—, $C_1$–$C_4$alkyl-$SO_2$—, $C_1$–$C_8$alkoxycarbonyl, $C_3$–$C_8$alkenyloxycarbonyl, $C_3$–$C_8$alkynyloxycarbonyl, $C_1$–$C_4$alkylideneaminooxy or $N(R_{10})(R_{11})$, or is $C_3$–$C_8$alkenyl;

$R_9$ alkyl, haloalkyl, CN or $C_1$–$C_4$alkoxycarbonyl;

and $R_{10}$ and $R_{11}$ are each independently of the other $C_1$–$C_8$alkyl, $C_3$–$C_8$alkenyl, $C_3$–$C_8$alkynyl, phenyl, benzyl or phenyl or benzyl, each substituted by halogen, $NO_2$, CN, $OCH_3$, or $CF_3$, or $R_{10}$ and $R_{11}$, together with the linking nitrogen atom, form a 5–7-membered saturated heterocycle.

10. A composition according to claim 9, which comprises a compound of formula III or IV

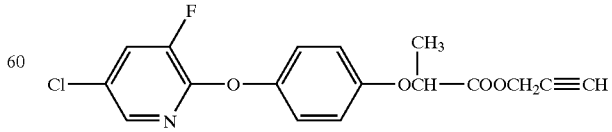

(III)

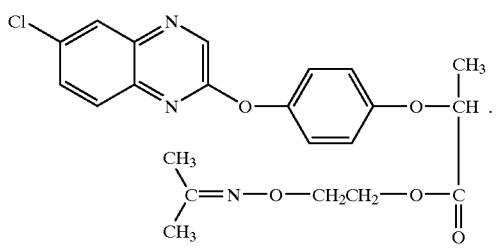
(IV)

11. A composition according to claim 10, which additionally comprises a compound of formula VIII

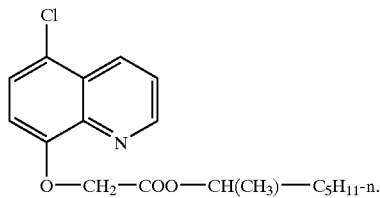
(VIII)

as safener.

12. A formulation according to claim 1, which contains the porous carrier material in an amount of 30 to 60% by weight, based on the total formulation.

13. A formulation according to claim 1, which contains the porous carrier material in an amount of 35 to 50% by weight, based on the total formulation.

14. A formulation according to claim 1, which contains the herbicide in an amount of 1 to 30% by weight, based on the total formulation.

15. A formulation according to claim 1, which contains the herbicide in an amount of 5 to 15% by weight, based on the total formulation.

16. A process for the preparation of a formulation as claimed in claim 1, which comprises mixing components a), b) and c) with one another.

17. A herbicidal composition, which contains a biologically active amount of the formulation as claimed in claim 1 dispersed in water.

18. A method of controlling weeds and grasses in crops of useful plants, which comprises treating said crops, the seeds or the crop area thereof with an effective amount of a herbicidal composition as claimed in claim 17.

* * * * *

UNITED STATES PATENT AND TRADEMARK OFFICE
CERTIFICATE OF CORRECTION

PATENT NO. : 6,656,883 B1  Page 1 of 1
DATED : December 2, 2003
INVENTOR(S) : Manfred Vogt et al.

It is certified that error appears in the above-identified patent and that said Letters Patent is hereby corrected as shown below:

Title page,
Item [*] Notice, should be deleted.

Signed and Sealed this

Seventeenth Day of August, 2004

JON W. DUDAS
*Acting Director of the United States Patent and Trademark Office*